United States Patent [19]

Irizawa et al.

[11] Patent Number: 5,612,388

[45] Date of Patent: Mar. 18, 1997

[54] POLYFUNCTIONAL CATIONIC MONOMER AND PROCESS FOR PRODUCING THE SAME

[75] Inventors: Tadashi Irizawa; Masahiko Morooka, both of Kanagawa; Masahiko Miyanoki, Tokyo, all of Japan

[73] Assignee: Nitto Chemical Industry Co., Ltd., Tokyo, Japan

[21] Appl. No.: 528,706

[22] Filed: Sep. 15, 1995

[30] Foreign Application Priority Data

Sep. 21, 1994 [JP] Japan .................................. 6-251563

[51] Int. Cl.⁶ .............................. C08F 2/46; C08F 12/34; C07C 233/00
[52] U.S. Cl. .............................. 522/6; 526/304; 526/310; 526/311; 526/312; 560/155
[58] Field of Search ..................................... 526/304, 310, 526/311, 312; 549/513, 551; 560/155; 522/6

[56] References Cited

U.S. PATENT DOCUMENTS

| 3,678,098 | 7/1972 | Lewis et al. | 526/312 |
| 4,218,554 | 8/1980 | Foley, Jr. | 526/312 |
| 4,560,599 | 12/1985 | Regen | 526/311 |
| 5,284,879 | 2/1994 | Hodgdon et al. | 526/310 |

*Primary Examiner*—Tae Yoon
*Attorney, Agent, or Firm*—Sughrue, Mion, Zinn, Macpeak & Seas

[57] ABSTRACT

A polyfunctional cationic monomer produced by reacting a tertiary amine having a polymerizable vinyl group with a compound having two or more oxirane groups. The polyfunctional cationic monomer of the present invention shows a very high curing rate and a high reaction suitability as a radiation cure coating to be applied onto the surface of a molded article made of plastics, wood, metals, etc. or the surface of a sheet such as a paper, a film, a metal plate, a knitted web, etc.

11 Claims, No Drawings

POLYFUNCTIONAL CATIONIC MONOMER AND PROCESS FOR PRODUCING THE SAME

FIELD OF THE INVENTION

This invention relates to a polyfunctional cationic monomer, a process for producing the same and a curable composition containing this monomer.

The polyfunctional cationic monomer according to the present invention is highly suitable, in particular, for a radiation-curable coating applied onto the surface of a molded article made of plastics, wood, metals, etc. or the surface of a sheet such as a paper, a film, a metal plate, a knitted web, etc.

BACKGROUND OF THE INVENTION

It is known in the art as a means for achieving a high productivity and giving a high performance to coat the surface of a molded article made of plastics, wood, metals, etc. or the surface of a sheet such as a paper, a film, a metal plate, a knitted web, etc. using radiation such as ultraviolet rays, visible rays or electron rays to thereby impart various functions to the surface.

By using this method, cationic organic atomic groups are introduced onto the surface of a material in order to impart particular functions (antistatic properties, dye-receptive properties, moisture absorption properties, water absorption properties, etc.) thereto. However, the cationic monomers manufactured industrially at present are restricted to monofunctional ones such as dimethylaminomethyl (meth)acrylate, (meth)acryloyloxyethyl-trimethyl-ammonium chloride, diallyl-dimethyl-ammonium chloride, dimethylaminopropyl (meth)acrylamide and (meth)acryloylaminopropyl-trimethyl-ammonium chloride.

In radiation-induced polymerization for the above-mentioned purposes, it is not appropriate to perform the polymerization and curing over such a long period of time as is done in the case of ordinary polymerization techniques. Instead, a highly reactive monomer with a short curing time is required. However, most of the cationic monomers manufactured industrially at present are monofunctional ones which are insufficient in polymerizablity. Accordingly, there has a need to develop a polyfunctional cationic monomer which is more suitable for these purposes.

SUMMARY OF THE INVENTION

An object of the present invention is to provide a polyfunctional cationic monomer as will be described herein, a process for producing the same and a curable composition containing this monomer.

DETAILED DESCRIPTION OF THE INVENTION

The polyfunctional cationic monomer of the present invention can be represented by formula (1):

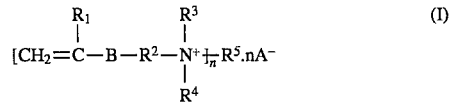

wherein $R^1$ represents a methyl group or a hydrogen atom; B represents —COO— or —CONH—; $R^2$ represents a divalent hydrocarbon group having from 2 to 8 carbon atoms, preferably a —$CH_2$—$CH_2$— group or a —$CH_2$—$CH_2$—$CH_2$— group; $R^3$ and $R^4$ each represents a hydrocarbon group having from 1 to 4 carbon atoms, preferably a methyl group; n is an integer of from 2 to 6; $R^5$ is an organic group having a valence of n; and A is an acid radical anion, preferably a polymerizable acid radical anion. In the above formula (1), examples of the organic group having a valence of n in $R^5$ is a group represented by formula:

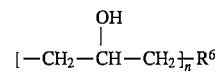

wherein n is an integer of from 2 to 6; and $R^6$ represents an organic group having a valence of n, preferably those represeted by the following formulae:

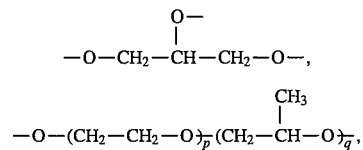

wherein p and q are each an integer of from 0 to 50, provided that the sum of p and q is from 1 to 50;

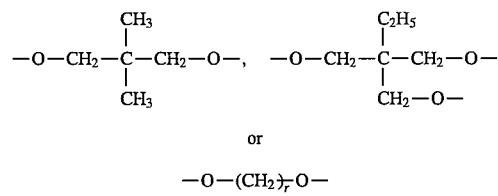

or $$-O-(CH_2)_r-O-$$

wherein r is an integer of from 2 to 6.

The polyfunctional cationic monomer of the present invention represented by the formula (1) can be obtained by reacting a tertiary amine having a polymerizable vinyl group represented by formula (2).

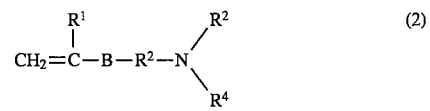

wherein $R^1$ represents a methyl group or a hydrogen atom; B represents a —COO— or —CONH— group; $R^2$ represents a divalent hydrocarbon group having from 2 to 8 carbon atoms; and $R^3$ and $R^4$ represent each a hydrocarbon group having from 1 to 4 carbon atoms; with a compound having two or more oxirane groups.

Typical examples of the tertiary amine having a polymerizable vinyl group represented by the general formula (2) in the present invention include but are not limited to acrylic acid esters or methacrylic acid esters such as N,N-dimethylaminomethyl acrylate, N,N-dimethylaminomethyl methacrylate, N,N-diethylaminomethyl acrylate and N,N-diethylaminomethyl methacrylate, acrylic acid amides or methacrylic acid amides such as N,N-dimethylaminopropylmethacrylamide, N,N-dimethylaminopropylacrylamide, N,N-dimethylaminoethylmethacrylamide and N-(-4-(N',N'-dimethylamino)-2-methyl-butyl-2-)acrylamide, and diallyl-methyl-amine.

The compound having two or more oxirane groups is, for example, a compound represented by formula (3):

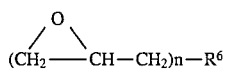

(3)

wherein n is an integer of from 2 to 6; and $R^6$ represents an organic group having a valence of n.

Preferred examples of $R^6$ in the above formula (3) are as follows:

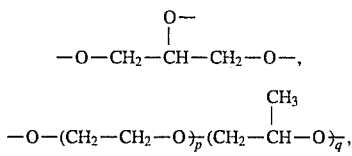

wherein p and q are each an integer of from 0 to 50, provided that the sum of p and q is from 1 to 50;

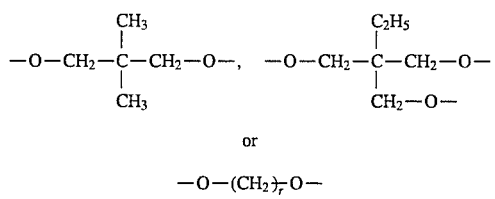

or $$-O-(CH_2)_r-O-$$

wherein r is an integer of from 2 to 6.

Typical examples of these compounds of the formula (3) include diglycidyl ethers such as ethylene glycol diglycidyl ether, 1,6-hexanediol diglycidyl ether, neopentyl glycol diglycidyl ether, polyethylene glycol diglycidyl ether, polypropylene glycol diglycidyl ether, resorcin diglycidyl ether and bisphenol A type epoxy resins, polyglycidyl ethers such as glycerol-polyglycidyl ether, trimethylolpropane polyglycidyl ether, phenol/novolak type epoxy resins, o-cresol novolak type epoxy resins and sorbitol polyglycidyl ether, and diglycidyl esters such as diglycidyl phthalate, diglycidyl hexahydrophthalate and heterocyclic epoxy compounds (e.g., triglycidyl isocyanurate).

Furthermore, examples of the compound having two or more oxirane groups other than those represented by the above formula (3) include epoxy compounds such as 3,4-epoxycyclohexylmethyl-3,4-epoxycyclohexyl carboxylate and vinylcyclohexene dioxide.

Among these compounds having two or more oxirane groups, one having a glycidyl group derived from epichlorohydrin usually has an epoxy equivalent exceeding the theoretical value, since it contains chlorohydroxypropyl or dihydroxypropyl groups which have been formed from some portion of glycidyl groups during the production process. The term "epoxy equivalent" as used herein means the average formula weight per epoxy group. In the present invention, such a compound containing chlorohydroxypropyl or dihydroxypropyl groups may be used as the compound having two or more oxirane groups, so long as it causes no problem in practice.

In order to conduct the present invention, the tertiary amine having a polymerizable vinyl group is usually neutralized with an equivalent amount of an acid prior to use. However, the acid may be used in excess or in a smaller amount.

Examples of the acid to be used for the neutralization include mineral acids such as hydrochloric acid, sulfuric acid and phosphoric acid, organic acids such as acetic acid, lactic acid, succinic acid, adipic acid, glutaric acid, sebacic acid, azelaic acid, decanedicarboxylic acid, thiodipropionic acid, phthalic acid and isophthalic acid, and polymerizable acids such as acrylic acid, methacrylic acid, itaconic acid, fumaric acid, maleic acid and 2-acrylamido-2-methylpropylsulfonic acid.

The polyfunctional cationic monomer is produced by mixing the tertiary amine having a polymerizable vinyl group represented by formula (2), which has been substantially neutralized, with the compound having two or more oxirane groups. For accelerating the reaction, the reaction temperature may be elevated.

In general, the tertiary amine having a polymerizable vinyl group and the compound having two or more oxirane groups are used in such a ratio that the equivalent of the tertiary amine is substantially the same as that of the epoxy group.

If necessary, a polar solvent such as water, dimethylformamide, dimethylacetamide, dimethyl sulfoxide, N-methylpyrrolidone, dioxane and acetonitrile may be used as a reaction medium.

If it is not desirable to use a polar solvent, a nonpolar hydrocarbon liquid, in which the target product is substantially insoluble, may be used as a dispersion medium. In such a case, various surfactants may be added to maintain the stable dispersion of fine particles.

To maintain the stability during the reaction and the qualities of the product, a polymerization inhibitor such as p-methoxyphenol or hydroquinone may be used.

The curable composition of the present invention comprises the polyfunctional cationic monomer represented by the above formula (1) optionally together with a photopolymerization initiator. In addition, the composition of the present invention may optionally contain other components selected from among various polymerizable monomers, various polymeric materials, media for regulating viscosity, surfactants, various coloring matters, fillers, durability improvers such as antioxidants and UV absorbers, etc., depending on the purpose of the composition.

Examples of the photopolymerization initiator, which is usable in the composition of the present invention, include acetophenone-series photopolymerization initiators, benzoin-series photopolymerization initiators, benzophenone-series photopolymerization initiators, thioxanthone-series photopolymerization initiators and acylphosphine oxide-series photopolymerization initiators. It is preferable to select an appropriate photopolymerization initiator by considering the efficiency of photopolymerization initiation, the stability of the composition, the compatibilities with the monomer(s) and the dilution medium, and the influence on the coating film after the completion of the photopolymerization, etc.

The acetophenone-series photopolymerization initiators are exemplified by benzyl methyl ketal, 2-hydroxy-2-methyl-1-phenylpropan-1-one, 1-hydroxycyclohexyl-phenyl ketone and 2-methyl-2-morpholino(4-thiomethylphenyl) propan-1-one. The benzoin-series photopolymerization initiators are exemplified by benzoin and benzoin ethyl ether. The benzophenone-series photopolymerization initiators are exemplified by methyl o-benzoylbenzoate and 4-benzoyl-N, N-dimethyl-N-[2(1-oxo-2-propenyloxy)ethyl]benzenemethanamium bromide. The thioxanthone-series photopolymerization initiators are exemplified by 2,4-diethylthioxanthone and 2-hydroxy-3-(3,4-dimethyl-9-oxo-9-H-thioxanthen-2-yloxy)-N,N,N-trimethyl-1-propanamium chloride. The acylphosphine oxide-series photopolymerization initiators are exemplified by 2,4,6-trimethylbenzoyldiphenylphosphine oxide. In addition, other photopolymerization initiators such as methyl phenylglyoxylate and camphor quinone/amine-series photopolymerization initiators may be used.

In general, an amine-series accelerator is used together with a benzoin-series or thioxanthone-series photopolymerization initiator. Examples of such amine-series accelerators include methyldiethanolamine and trimethanolamine.

Examples of the polymerizable monomers which can be combined with the composition of the present invention include various vinyl compounds such as acrylic acid salts, methacrylic acid salts, acrylic acid esters, methacrylic acid esters, vinyl esters, vinyl ethers, acrylamides, methacrylamides, sodium vinylsulfonate, sodium methacrylsulfonate, acrylonitrile, methacrylonitrile, diallyldimethyl ammonium chloride, N-vinylpyrrolidone, N-vinylcaprolactam, N-vinylformamide and N-vinylacetamide, and polyfunctional monomers thereof.

The acrylic acid salts and methacrylic acid salts are exemplified by sodium salts, potassium salts and aluminum salts. The acrylic acid esters and methacrylic acid esters are exemplified by esters of the corresponding alcohols (for example, methyl, ethyl, hydroxyethyl, hydroxypropyl, dihydroxypropyl, glycidyl, alkyl polyethylene glycol, N,N-dimethylaminoethyl, allyl, propyl butyl, 2-ethylhexyl and tetrahydrofurfuryl alcohols), methacryloyloxyethyl trimethyl ammonium chloride and acryloyloxyethyl trimethyl ammonium chloride. The acrylamides and methacrylamides are exemplified by unsubstituted ones, N-tert-butyl(meth)acrylamide, N-tert-octyl(meth)acrylamide, N,N-dimethyl-(meth)acrylamide, N-methylol(meth)acrylamide, metoxymethyl(meth)acrylamide, butoxymethyl(meth)acrylamide, polyethylene glycol oxymethyl(meth)acrylamide, acrylamide glycolate (an adduct of acrylamide and glyoxalic acid), acryloyl morpholine and diacetone acrylamide. The vinyl esters are exemplified by vinyl acetate. The vinyl ethers are exemplified by vinyl methyl ether and vinyl isobutyl ether. As the polyfunctional monomers, esters of acrylic acid or methacrylic acid with polyhydric alcohols such as ethylene glycol, diethylene glycol, butanediol, hexanediol, polyethylene glycol, neopentyl glycol, trimethylolpropane, pentaerythritol and dipentaerythritol, various additives of acrylic acid or methacrylic acid with polyepoxy compounds such as bisphenol A-type epoxy resins or novolak-type epoxy resins, urethane-modified polyfunctional acrylates and methylenebisacrylamide may be used.

Examples of the polymeric materials which are usable in the composition of the present invention include cationic polymers produced by polymerizing cationic monomers such as N,N-dimethylaminomethyl acrylate, N,N-dimethylaminomethyl methacrylate, N,N-diethylaminomethyl acrylate, N,N-diethylaminomethyl methacrylate, N,N-dimethylaminopropylmethacrylamide, N,N-dimethylaminopropylacrylamide, N,N-dimethylaminoethylmethacrylamide, N-(-4-(N',N'-dimethylamino)-2-methyl-butyl-2-)acrylamide, methacryloyloxyethyl-trimethylammonium chloride, acryloyloxymethyl-trimethyl ammonium chloride, methacryloylaminopropyl-trimethyl ammonium chloride, acryloylaminopropyl-trimethyl ammonium chloride and diallyldimethyl ammonium chloride, polyvinyl alcohol, sodium polyacrylate, starch and various polysaccharides.

Examples of the media for regulating viscosity which are usable in the composition of the present invention include polar solvents such as water, alcohols, dimethyl sulfoxide, dimethylacetamide, N-methylpyrrolidone, dioxane and acetonitrile. In the case of an oil-soluble composition, alcohols, esters, ethers, hydrocarbons, etc. may be used.

The present invention will now be illustrated in greater detail with reference to the Examples, but should not be construed as being limited thereto. All of parts and percents are given by weight unless otherwise indicated.

EXAMPLE 1

Adduct of glycerol polyglycidyl ether and dimethylaminoethyl acrylate/lactic acid salt:

Into a 500 ml separable flask provided with a thermometer, a stirrer, a reflux condenser and a drop measuring tank was fed 118.5 g (1.0 mol) of 76% lactic acid (containing 12.7% of water and 11.3% of a nonacidic lactic acid condensate). Then 157.2 g (1.0 mol) of dimethylaminoethyl methacrylate was dropped thereinto for 30 minutes while maintaining the temperature in the flask at 16° to 20° C. to thereby synthesize dimethylaminoethyl methacrylate lactic acid salt.

Subsequently, 145 g of glycerol polyglycidyl ether (epoxy equivalent: 145, chlorine content: 11.5%) was dropped thereinto for 30 minutes while maintaining the temperature in the reaction system at 55° to 65° C. Then the reaction mixture was stirred for 5 hours while maintaining the temperature in the reaction system at 60° to 65° C.

A portion of the product thus obtained was sampled and the double bond remaining therein was determined in accordance with the Bromide-Bromate method described in JIS-K-6716 (1977). As a result, the value thus determined corresponded to 99% of the theoretical value.

The reaction product was introduced into a pyrex test tube (diameter: 5 mm) and the NMR spectra were measured with the use of an NMR spectrometer (Model JNM-GX270, manufactured by JEOL Ltd.). The measurement frequencies for $^1H$ and $^{13}C$ spectra were respectively 270 MHz and 68 MHz. Dimethyl sulfoxide-$d_6$ was used as a measurement solvent, while tetramethylsilane was used as a standard.

The $^1H$-NMR spectrum thus obtained showed no doublet at $\delta=2.5$–3.0, i.e., a peak derived from $CH_2$ in the oxirane ring of the glycidyl group in the starting material, which indicated that all glycidyl groups had been reacted and thus lost. In the $^1H$-NMR spectrum, further, the chemical shift $\delta=2.3$–2.8 derived from N-$CH_3$ shifted to $\delta=3.2$–3.3 derived from $N^+$—$CH_3$, which indicated that dimethylaminoethyl groups (i.e., the tertiary amine groups) in the starting material had been reacted and lost. In the $^{13}C$-NMR spectrum of the product, the chemical shift of a peak derived from $N^+$—$CH_3$ was located at $\delta=52$–53, which proved that quaternary ammonium groups had been formed.

These results of the analysis suggested that the target product was formed at an extremely high yield.

A mixture comprising 85 parts by weight of the polyfunctional cationic monomer thus obtained, 15 parts by weight of pure water and 1 part by weight of benzoin ethyl ether (a photopolymerization initiator) was applied onto a coat paper with a screen printing machine in such a manner as to give a film thickness of about 20 μm. Then it was irradiated with an UV irradiation lamp (80 W/cm) located 10 cm apart therefrom at a rate of 2 m/min. After the irradiation, the surface of the coating was neither flowable nor sticky, which indicated that it had been cured sufficiently.

EXAMPLE 2

Adduct of glycerol polyglycidyl ether and dimethylaminoethyl acrylate/lactic acid salt:

Into a 500 ml separable flask provided with a thermometer, a stirrer, a reflux condenser and a drop measuring tank was fed 118.5 g (1.0 mol) of 76% lactic acid (containing 12.7% of water and 11.3% of a nonacidic lactic acid condensate). Then 143.2 g (1.0 mol) of dimethylaminoethyl acrylate was dropped thereinto for 30 minutes while maintaining the temperature in the flask at 16° to 20° C. to thereby synthesize dimethylaminoethyl acrylate lactic acid salt.

Subsequently, 156 g of glycerol polyglycidyl ether (epoxy equivalent: 145, chlorine content: 11.5%) was dropped thereinto for 30 minutes while maintaining the temperature in the reaction system at 55° to 65° C. Then the reaction mixture was stirred for 7 hours while maintaining the temperature in the reaction system at 60° to 65° C.

A portion of the product thus obtained was sampled and the double bond remaining therein was determined by the same method as described in Example 1. As a result, the value thus determined corresponded to 98% of the theoretical value.

A mixture comprising 85 parts by weight of the polyfunctional cationic monomer thus obtained, 15 parts by weight of pure water and 1 part by weight of benzoin ethyl ether (a photopolymerization initiator) was applied onto a coat paper with a screen printing machine in such a manner as to give a film thickness of about 20 μm. Then it was irradiated with an UV irradiation lamp (80 W/cm) located 10 cm apart therefrom at a rate of 2 m/min. After the irradiation, the surface of the coating was neither flowable nor sticky, which indicated that it had been cured sufficiently.

EXAMPLE 3

Adduct of polyethylene glycol diglycidyl ether and dimethylaminoethyl acrylate/lactic acid salt:

Into a 500 ml separable flask provided with a thermometer, a stirrer, a reflux condenser and a drop measuring tank was fed 118.5 g (1.0 mol) of 76% lactic acid (containing 12.7% of water and 11.3% of a nonacidic lactic acid condensate). Then 143.2 g (1.0 mol) of dimethylaminoethyl acrylate was dropped thereinto for 30 minutes while maintaining the temperature in the flask at 16° to 20° C. to thereby synthesize dimethylaminoethyl acrylate lactic acid salt.

Subsequently, 262 g of polyethylene glycol diglycidyl ether (epoxy equivalent: 262, chlorine content: 1%, obtained by converting polyethylene glycol of average molecular weight of 415 into diglycidyl ether) was dropped thereinto for 30 minutes while maintaining the temperature in the reaction system at 55° to 65° C. Then the reaction mixture was stirred for 9 hours while maintaining the temperature in the reaction system at 60° to 65° C.

A portion of the product thus obtained was sampled and the double bond remaining therein was determined by the same method as described in Example 1. As a result, the value thus determined corresponded to 98% of the theoretical value.

EXAMPLE 4

Adduct of glycerol polyglycidyl ether and N-dimethylaminopropyl methacrylamide/lactic acid salt:

Into a 500 ml separable flask provided with a thermometer, a stirrer, a reflux condenser and a drop measuring tank was fed 118.5 g (1.0 mol) of 76% lactic acid (containing 12.7% of water and 11.3% of a nonacidic lactic acid condensate). While maintaining the temperature in the flask at 16° to 20° C., 33.7 g of pure water was first added thereto and then 171 g (1.0 mol) of N-dimethylaminopropylmethacrylamide was dropped thereinto for 30 minutes to thereby synthesize N-dimethylaminopropylmethacrylamide lactic acid salt.

Subsequently, 145 g of glycerol polyglycidyl ether (epoxy equivalent: 145, chlorine content: 11.5%) was dropped thereinto for 30 minutes while maintaining the temperature in the reaction system at 55° to 65° C. Then the reaction mixture was stirred for 7 hours while maintaining the temperature in the reaction system at 60° to 65° C.

A portion of the product thus obtained was sampled and the double bond remaining therein was determined by the same method as described in Example 1. As a result, the value thus determined corresponded to 99% of the theoretical value.

A mixture comprising 85 parts by weight of the polyfunctional cationic monomer thus obtained, 15 parts by weight of pure water and 1 part by weight of benzoin ethyl ether (a photopolymerization initiator) was applied onto a coat paper with a screen printing machine in such a manner as to give a film thickness of about 20 μm. Then it was irradiated with a UV irradiation lamp (80 W/cm) located 10 cm apart therefrom at a rate of 2 m/min. After the irradiation, the surface of the coating was neither flowable nor sticky, which indicated that it had been cured sufficiently.

EXAMPLE 5

Adduct of polyethylene glycol diglycidyl ether and N-dimethylaminopropylmethacrylamide/lactic acid salt:

Into a 500 ml separable flask provided with a thermometer, a stirrer, a reflux condenser and a drop measuring tank was fed 118.5 g (1.0 mol) of 76% lactic acid (containing 12.7% of water and 11.3% of a nonacidic lactic acid condensate). While maintaining the temperature in the flask at 16° to 20° C., 33.7 g of pure water was first added thereto and then 171 g (1.0 mol) of N-dimethylaminopropylmethacrylamide was dropped thereinto for 30 minutes to thereby synthesize N-dimethylaminopropylmethacrylamide lactic acid salt.

Subsequently, 262 g of polyethylene glycol diglycidyl ether (epoxy equivalent: 262, chlorine content: 1%) was dropped thereinto for 30 minutes while maintaining the temperature in the reaction system at 55° to 65° C. Then the reaction mixture was stirred for 7 hours while maintaining the temperature in the reaction system at 60° to 65° C.

A portion of the product thus obtained was sampled and the double bond remaining therein was determined by the same method as described in Example 1. As a result, the value thus determined corresponded to 98% of the theoretical value.

EXAMPLE 6

Adduct of polyethylene glycol diglycidyl ether and dimethylaminoethyl methacrylate/lactic acid salt:

Into a 500 ml separable flask provided with a thermometer, a stirrer, a reflux condenser and a drop measuring tank was fed 118.5 g (1.0 mol) of 76% lactic acid (containing 12.7% of water and 11.3% of a nonacidic lactic acid condensate). While maintaining the temperature in the flask at 16° to 20° C., 157.2 g (1.0 mol) of dimethylaminoethyl methacrylate was dropped thereinto for 30 minutes to thereby synthesize dimethylaminoethyl methacrylate lactic acid salt.

Subsequently, 262 g of polyethylene glycol diglycidyl ether (epoxy equivalent: 262, chlorine content: 1%, obtained by converting polyethylene glycol of average molecular weight of 415 into diglycidyl ether) was dropped thereinto for 30 minutes while maintaining the temperature in the reaction system at 55° to 65° C. Then the reaction mixture was stirred for 9 hours while maintaining the temperature in the reaction system at 60° to 65° C.

A portion of the product thus obtained was sampled and the double bond remaining therein was determined by the same method as described in Example 1. As a result, the value thus determined corresponded to 97% of the theoretical value.

EXAMPLE 7

Adduct of polyethylene glycol diglycidyl ether and dimethylaminoethyl methacrylate/succinic acid salt:

Into a 500 ml separable flask provided with a thermometer, a stirrer, a reflux condenser and a drop measuring tank were fed 59 g of pure water and 59.1 g (0.5 mol) of succinic acid. While maintaining the temperature in the flask at 16° to 20° C., 157.2 g (1.0 mol) of dimethylaminoethyl methacrylate was dropped thereinto for 30 minutes to thereby synthesize dimethylaminoethyl methacrylate succinic acid salt.

Subsequently, 262 g of polyethylene glycol diglycidyl ether (epoxy equivalent: 262, chlorine content: 1%, obtained by converting polyethylene glycol of average molecular weight of 415 into diglycidyl ether) was dropped thereinto for 30 minutes while maintaining the temperature in the reaction system at 55° to 65° C. Then the reaction mixture was stirred for 8 hours while maintaining the temperature in the reaction system at 60° to 65° C.

A portion of the product thus obtained was sampled and the double bond remaining therein was determined by the same method as described in Example 1. As a result, the value thus determined corresponded to 95% of the theoretical value.

A mixture comprising 20 parts by weight of the polyfunctional cationic monomer thus obtained, 30 parts by weight of hydroxyethyl methacrylate, 50 parts by weight of pure water and 2,2'-azobis(2-amidinopropane) hydrochloride (a polymerization initiator) was introduced into a test tube. After purging oxygen in the tube with nitrogen, the mixture was heated to 60° C. for 8 hours. After cooling, the product taken out from the test tube was in the form of a hydrogel insoluble in water.

EXAMPLE 8

Adduct of polyethylene glycol diglycidyl ether and dimethylaminoethyl methacrylate/sulfuric acid salt:

Into a 500 ml separable flask provided with a thermometer, a stirrer, a reflux condenser and a drop measuring tank were fed 88 g of pure water and 50 g (0.5 mol) of conc. sulfuric acid. While maintaining the temperature in the flask at 16° to 20° C., 157.2 g (1.0 mol) of dimethylaminoethyl methacrylate was dropped thereinto for 30 minutes to thereby synthesize dimethylaminoethyl methacrylate sulfuric acid salt.

Subsequently, 262 g of polyethylene glycol diglycidyl ether (epoxy equivalent: 262, chlorine content: 1%, obtained by converting polyethylene glycol of average molecular weight of 415 into diglycidyl ether) was dropped thereinto for 30 minutes while maintaining the temperature in the reaction system at 55° to 65° C. Then the reaction mixture was stirred for 8 hours while maintaining the temperature in the reaction system at 60° to 65° C.

A portion of the product thus obtained was sampled and the double bond remaining therein was determined by the same method as described in Example 1. As a result, the value thus determined corresponded to 97% of the theoretical value.

EXAMPLE 9

Adduct of polyethylene glycol diglycidyl ether and dimethylaminoethyl methacrylate/phosphoric acid salt:

Into a 500 ml separable flask provided with a thermometer, a stirrer, a reflux condenser and a drop measuring tank were fed 27 g of pure water and 25.3 g (0.22 mol) of 85% phosphoric acid. While maintaining the temperature in the flask at 16° to 20° C., 104 g (0.66 mol) of dimethylaminoethyl methacrylate was dropped thereinto for 30 minutes to thereby synthesize dimethylaminoethyl methacrylate phosphoric acid salt.

Subsequently, 175 g of polyethylene glycol diglycidyl ether (epoxy equivalent: 262, chlorine content: 1%, obtained by converting polyethylene glycol of average molecular weight of 415 into diglycidyl ether) was dropped thereinto for 30 minutes while maintaining the temperature in the reaction system at 55° to 65° C. Then the reaction mixture was stirred for 8 hours while maintaining the temperature in the reaction system at 60° to 65° C.

A portion of the product thus obtained was sampled and the double bond remaining therein was determined by the same method as described in Example 1. As a result, the value thus determined corresponded to 97% of the theoretical value.

A solution was prepared by thoroughly mixing 15 parts by weight of the polyfunctional cationic monomer thus obtained, 15 parts by weight of polyethylene glycol diacrylate (n=4), 30 parts by weight of hydroxyethyl methacrylate, 50 parts by weight of pure water and 0.5 parts by weight of 2,4,6-trimethylbenzoyldiphenylphosphine oxide (a photopolymerization initiator). Next, a mold (10 cm×10 cm), which had been prepared by hollowing out a Teflon sheet (thickness: 1 mm), was placed on a glass plate and the abovementioned solution was poured thereinto. Then it was covered with a polyethylene terephthalate film (thickness: 100 μm) and irradiated with a blue fluorescent lamp (FL-20S-B, manufactured by Toshiba Co.) located 20 cm apart therefrom for 30 minutes. After removing the polyethylene terephthalate film, the sheet product taken out from the mold was in the form of a soft hydrogel which was insoluble in water.

EXAMPLE 10

Adduct of polyethylene glycol diglycidyl ether and dimethylaminoethyl methacrylate/2-acrylamido-2-methylpropanesulfonic acid salt:

Into a 500 ml separable flask provided with a thermometer, a stirrer, a reflux condenser and a drop measuring tank were fed 43 g of pure water and 78.8 g (0.5 mol) of dimethylaminoethyl methacrylate. While maintaining the temperature in the flask at 16° to 20° C., 105.2 g (0.5 mol) of 2-acrylamido-2-methylpropanesulfonic acid was dropped thereinto for 30 minutes to thereby synthesize dimethylaminoethyl methacrylate 2-acrylamido-2-methylpropanesulfonic acid salt.

Subsequently, 131 g of polyethylene glycol diglycidyl ether (epoxy equivalent: 262, chlorine content: 1%, obtained by converting polyethylene glycol of average molecular weight of 415 into diglycidyl ether) was dropped thereinto for 30 minutes while maintaining the temperature in the reaction system at 55° to 65° C. Then the reaction mixture was stirred for 15 hours while maintaining the temperature in the reaction system at 60° to 65° C.

A portion of the product thus obtained was sampled and the double bond remaining therein was determined by the same method as described in Example 1. As a result, the value thus determined corresponded to 98% of the theoretical value.

EXAMPLE 11

Adduct of trimethylolporpane polyglycidyl ether and dimethylaminoethyl methacrylate/succinic acid salt:

Into a 500 ml separable flask provided with a thermometer, a stirrer, a reflux condenser and a drop measuring tank were fed 59 g of pure water and 59.1 g (0.5 mol) of succinic acid. While maintaining the temperature in the flask at 16° to 20° C., 157.2 g (1.0 mol) of dimethylaminoethyl methacrylate was dropped thereinto for 30 minutes to thereby synthesize dimethylaminoethyl methacrylate succinic acid salt.

Subsequently, 145 g of trimethylolpropane polyglycidyl ether (epoxy equivalent: 145, chlorine content: 8%) was dropped thereinto for 30 minutes while maintaining the temperature in the reaction system at 55° to 65° C. Then the reaction mixture was stirred for 8 hours while maintaining the temperature in the reaction system at 60° to 65° C.

A portion of the product thus obtained was sampled and the double bond remaining therein was determined by the same method as described in Example 1. As a result, the value thus determined corresponded to 97% of the theoretical value.

EXAMPLE 12

Adduct of trimethylolporpane polyglycidyl ether and dimethylaminoethyl methacrylate/lactic acid salt:

Into a 500 ml separable flask provided with a thermometer, a stirrer, a reflux condenser and a drop measuring tank was fed 59.3 g (0.5 mol) of 76% lactic acid (containing 12.7% of water and 11.3% of a nonacidic lactic acid condensate). While maintaining the temperature in the flask at 16° to 20° C., 78.6 g (0.5 mol) of dimethylaminoethyl methacrylate was dropped thereinto for 30 minutes to thereby synthesize dimethylaminoethyl methacrylate lactic acid salt.

Subsequently, 72.5 g of trimethylolpropane polyglycidyl ether (epoxy equivalent: 145, chlorine content: 8%) was dropped thereinto for 30 minutes while maintaining the temperature in the reaction system at 55° to 65° C. Then the reaction mixture was stirred for 8 hours while maintaining the temperature in the reaction system at 60° to 65° C. After the completion of the reaction, 30 g of pure water was added to thereby make the viscous reaction mixture easy to handle.

A portion of the product thus obtained was sampled and the double bond remaining therein was determined by the same method as described in Example 1. As a result, the value thus determined corresponded to 99% of the theoretical value.

EXAMPLE 13

Adduct of neopentyl glycol diglycidyl ether and dimethylaminoethyl methacrylate/succinic acid salt:

Into a 500 ml separable flask provided with a thermometer, a stirrer, a reflux condenser and a drop measuring tank were fed 59 g of pure water and 59.1 g (0.5 mol) of succinic acid. While maintaining the temperature in the flask at 16° to 20° C., 157.2 g (1.0 mol) of dimethylaminoethyl methacrylate was dropped thereinto for 30 minutes to thereby synthesize dimethylaminoethyl methacrylate succinic acid salt.

Subsequently, 140 g of neopentyl glycol diglycidyl ether (epoxy equivalent: 140, chlorine content: 5.4%) was dropped thereinto for 30 minutes while maintaining the temperature in the reaction system at 55° to 65° C. Then the reaction mixture was stirred for 8 hours while maintaining the temperature in the reaction system at 60° to 65° C.

A portion of the product thus obtained was sampled and the double bond remaining therein was determined by the same method as described in Example 1. As a result, the value thus determined corresponded to 97% of the theoretical value.

EXAMPLE 14

Adduct of 1,6-hexanediol diglycidyl ether and dimethylaminoethyl methacrylate/succinic acid salt:

Into a 500 ml separable flask provided with a thermometer, a stirrer, a reflux condenser and a drop measuring tank were fed 59 g of pure water and 59.1 g (0.5 mol) of succinic acid. While maintaining the temperature in the flask at 16° to 20° C., 157.2 g (1.0 mol) of dimethylaminoethyl methacrylate was dropped thereinto for 30 minutes to thereby synthesize dimethylaminoethyl methacrylate succinic acid salt.

Subsequently, 150 g of 1,6-hexanediol diglycidyl ether (epoxy equivalent: 150, chlorine content: 6.3%) was dropped thereinto for 30 minutes while maintaining the temperature in the reaction system at 55° to 65° C. Then the reaction mixture was stirred for 8 hours while maintaining the temperature in the reaction system at 60° to 65° C.

A portion of the product thus obtained was sampled and the double bond remaining therein was determined by the same method as described in Example 1. As a result, the value thus determined corresponded to 99% of the theoretical value.

EXAMPLE 15

Adduct of resorcin diglycidyl ether and dimethylaminoethyl methacrylate/succinic acid salt:

Into a 500 ml separable flask provided with a thermometer, a stirrer, a reflux condenser and a drop measuring tank were fed 80 g of acetonitrile and 29.5 g (0.25 mol) of succinic acid. While maintaining the temperature in the flask at 16° to 20° C., 78.6 g (0.5 mol) of dimethylaminoethyl methacrylate was dropped thereinto for 30 minutes to thereby synthesize dimethylaminoethyl methacrylate succinic acid salt.

Subsequently, a mixture of 59 g of resorcin diglycidyl ether (epoxy equivalent: 118) with 50 g of acetonitrile was dropped thereinto for 30 minutes while maintaining the temperature in the reaction system at 55° to 65° C. Then the reaction mixture was stirred for 8 hours while maintaining the temperature in the reaction system at 60° to 65° C. After adding 30 g of pure water, the reaction system was evacuated and the major part of the acetonitrile added was evaporated for about 4 hours.

A portion of the product thus obtained was sampled and the double bond remaining therein was determined by the same method as described in Example 1. As a result, the value thus determined corresponded to 97% of the theoretical value.

A mixture comprising 40 parts by weight of the polyfunctional cationic monomer thus obtained, 45 parts by weight of polyethylene glycol diacrylate (n=9), 15 parts by weight of pure water and 1 part by weight of benzoin ethyl ether (a photopolymerization initiator) was applied onto a surface-modified polyethylene terephthalate film (thickness: 70 µm)

with a screen printing machine in such a manner as to give a film thickness of about 20 μm. Then it was irradiated with a UV irradiation lamp (80 W/cm) located 10 cm apart therefrom at a rate of 2 m/min. After the irradiation, the surface of the coating was neither flowable nor sticky, which indicated that it had been cured sufficiently.

EXAMPLE 16

Adduct of bisphenol A type epoxy resin and dimethylaminoethyl methacrylate/succinic acid salt:

Into a 500 ml separable flask provided with a thermometer, a stirrer, a reflux condenser and a drop measuring tank were fed 80 g of acetonitrile and 29.5 g (0.25 mol) of succinic acid. While maintaining the temperature in the flask at 16° to 20° C., 78.6 g (0.5 mol) of dimethylaminoethyl methacrylate was dropped thereinto for 30 minutes to thereby synthesize dimethylaminoethyl methacrylate succinic acid salt.

Subsequently, a mixture of 93 g of bisphenol A type epoxy resin (epoxy equivalent: 186) with 50 g of acetonitrile was dropped thereinto for 30 minutes while maintaining the temperature in the reaction system at 55° to 65° C. Then the reaction mixture was stirred for 10 hours while maintaining the temperature in the reaction system at 60° to 65° C. After adding 30 g of pure water, the reacting system was evacuated and the major part of the acetonitrile added was evaporated for about 4 hours.

A portion of the product thus obtained was sampled and the double bond remaining therein was determined by the same method as described in Example 1. As a result, the value thus determined corresponded to 96% of the theoretical value.

EXAMPLE 17

Adduct of polyethylene glycol diglycidyl ether and dimethylaminoethyl methacrylate/acrylic acid salt:

Into a 1,000 ml separable flask provided with a thermometer, a stirrer, a reflux condenser and a drop measuring tank was fed 73.5 g (1 mol) of 98% acrylic acid. While maintaining the temperature in the flask at 16° to 20° C., 157.2 g (1.0 mol) of dimethylaminoethyl methacrylate was added thereto for 30 minutes.

Subsequently, 262 g of polyethylene glycol diglycidyl ether (epoxy equivalent: 262, chlorine content: 1%, obtained by converting polyethylene glycol of average molecular weight of 415 into diglycidyl ether) was dropped thereinto for 30 minutes while maintaining the temperature in the reaction system at 55° to 65° C. Then the reaction mixture was stirred for 14 hours while maintaining the temperature in the reaction system at 60° to 65° C.

A portion of the product thus obtained was sampled and the double bond remaining therein was determined by the same method as described in Example 1. As a result, the value thus determined corresponded to 95% of the theoretical value.

EXAMPLE 18

Adduct of sorbitol polyglycidyl ether and dimethylaminoethyl methacrylate/lactic acid salt:

Into a 500 ml separable flask provided with a thermometer, a stirrer, a reflux condenser and a drop measuring tank was fed 118.5 g (1.0 mol) of 76% lactic acid (containing 12.7% of water and 11.3% of a nonacidic lactic acid condensate). While maintaining the temperature in the flask at 16° to 20° C., 157.2 g (1.0 mol) of dimethylaminoethyl methacrylate was dropped thereinto for 30 minutes to thereby synthesize dimethylaminoethyl methacrylate lactic acid salt.

Subsequently, 180 g of sorbitol polyglycidyl ether (epoxy equivalent: 180) was dropped thereinto for 30 minutes while maintaining the temperature in the reaction system at 55° to 65° C. Then the reaction mixture was stirred for 8 hours while maintaining the temperature in the reaction system at 60° to 65° C.

A portion of the product thus obtained was sampled and the double bond remaining therein was determined by the same method as described in Example 1. As a result, the value thus determined corresponded to 98% of the theoretical value.

In the above Examples 2 to 18, the NMR spectra of the reaction products were measured in the same manner as described in Example 1. As a result, it was confirmed in each Examples that all of the glycidyl groups had been reacted and lost, and the dimethylaminoethyl groups in the tertiary amine groups had been reacted and lost while quaternary ammonium groups had been formed as a substitute therefor.

These analytical data indicated that the target product was formed at an extremely high yield in each of these Examples.

The polyfunctional cationic monomer of the present invention shows a very high curing rate and a high reaction suitability as a radiation cure coating to be applied onto the surface of a molded article made of plastics, wood, metals, etc. or the surface of a sheet such as a paper, a film, a metal plate, a knitted web, etc.

While the invention has been described in detail and with reference to specific embodiments thereof, it will be apparent to one skilled in the art that various changes and modifications can be made therein without departing from the spirit and scope thereof.

What is claimed is:

1. A polyfunctional cationic monomer represented by formula (1):

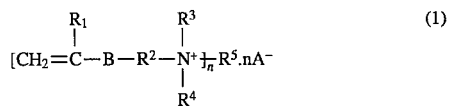

wherein $R^1$ represents a methyl group or a hydrogen atom; B represents a —COO— group or a —CONH— group; $R^2$ represents a divalent hydrocarbon group having 2 to 8 carbon atoms; $R^3$ and $R^4$ each represents a hydrocarbon group having 1 to 4 carbon atoms; n is an integer of from 2 to 6; $R^5$ is an organic group having a valence of n; and A is an acid radical anion.

2. A polyfunctional cationic monomer as claimed in claim 1, wherein $R^5$ is a group represented by formula:

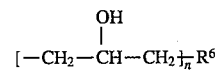

wherein n is an integer as defined above; and $R^6$ represents an organic group having a valence of n.

3. A polyfunctional cationic monomer as claimed in claim 2, wherein $R^6$ is selected from the group represented by the following formulae:

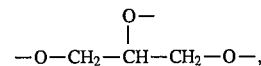

-continued

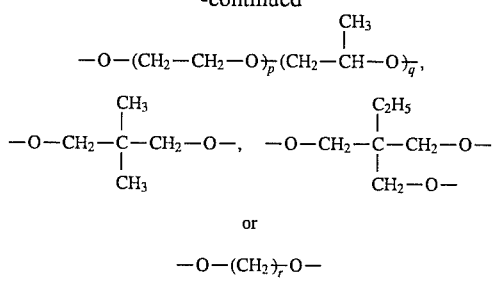

wherein p and q each is an integer of from 0 to 50, provided that the sum of p and q is from 1 to 50; and r is an integer of from 2 to 6.

4. A polyfunctional cationic monomer as claimed in claim 1, wherein $R^2$ is a —$CH_2$—$CH_2$— group or a —$CH_2$—$CH_2$—$CH_2$— group.

5. A polyfunctional cationic monomer as claimed in claim 1, wherein $R^3$ and $R^4$ each is a methyl group.

6. A polyfunctional cationic monomer as claimed in claim 1, wherein A is a polymerizable acid radical anion.

7. A polymerizable, curable composition, which contains a polyfunctional cationic monomer as claimed in any one of claims 1 to 6.

8. A photocurable composition, which contains a polyfunctional cationic monomer as claimed in any one of claims 1 to 6 and a photopolymerization initiator.

9. A process for producing a polyfunctional cationic monomer as claimed in claim 1, which comprises:

reacting a tertiary amine having a polymerizable vinyl group represented by formula (2):

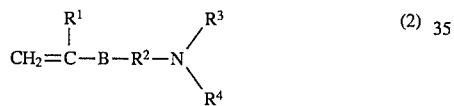

wherein $R^1$ represents a methyl group or a hydrogen atom; B represents a —COO— group or a —CONH— group; $R^2$ represents a divalent hydrocarbon group having 2 to 8 carbon atoms; and $R^3$ and $R^4$ each represents a hydrocarbon group having 1 to 4 carbon atoms;

with a compound having at least two oxirane groups.

10. A process for producing a polyfunctional cationic monomer as claimed in claim 9, wherein said compound having two or more oxirane groups is one represented by formula (3):

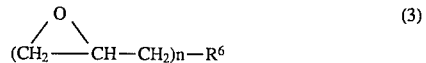

wherein n is an integer of from 2 to 6; and $R^6$ represents an organic group having a valence of n.

11. A process for producing a polyfunctional cationic monomer as claimed in claim 10, wherein $R^6$ is selected from the groups represented by the following formulae:

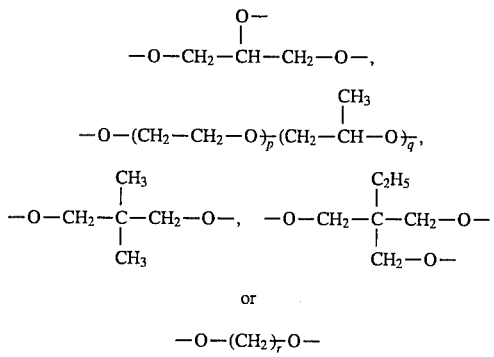

wherein p and q each is an integer of from 0 to 50, provided that the sum of p and q is from 1 to 50; and r is an integer of from 2 to 6.

* * * * *